United States Patent [19]

Kinsella et al.

[11] Patent Number: 5,192,677
[45] Date of Patent: Mar. 9, 1993

[54] ALKALI AND HEAT STABLE PROTEASE FROM THERMOMONOSPORA FUSCA

[75] Inventors: John E. Kinsella; Todd W. Gusek; David B. Wilson, all of Ithaca, N.Y.

[73] Assignee: Cornell Research Foundation Inc., Ithaca, N.Y.

[21] Appl. No.: 713,602

[22] Filed: Jun. 11, 1991

Related U.S. Application Data

[63] Continuation of Ser. No. 174,168, Mar. 28, 1988, which is a continuation-in-part of Ser. No. 930,090, Nov. 13, 1986, abandoned, which is a continuation-in-part of Ser. No. 860,934, May 8, 1986, abandoned.

[51] Int. Cl.$^5$ .................. C12N 9/52; C12N 9/50
[52] U.S. Cl. ..................................... 435/220; 435/219
[58] Field of Search .................. 435/212, 219, 220

[56] References Cited

U.S. PATENT DOCUMENTS

| | | | |
|---|---|---|---|
| 3,692,631 | 9/1972 | Larson et al. | 195/66 R |
| 4,364,926 | 12/1982 | Yokogawa et al. | 424/50 |
| 4,480,036 | 10/1984 | Morgan et al. | 435/220 |

OTHER PUBLICATIONS

Upton, M. E. et al. (1977) Appl. Environ. Michrobiol. 33(1), 59–64.
Stutzenberger, F. J., et al. (1982) Chem. Abst. 96:212963y.
Stutzenberger, F., Journal of Bacteriology, Jun. 1987, pp. 2774–2780.
Stutzenberger & Lawson, Biotechnology and Bioengineering, vol. XXIV, pp. 999–1006, (1982).
McCarthy & Cross, Journal of General Microbiology (1984), 130, 5–25.
Kristjansson, M. M., et al. (1990) Int. J. Peptide Protein Res. 29, preprint.

*Primary Examiner*—Charles L. Patterson, Jr.
*Attorney, Agent, or Firm*—Sughrue, Mion, Zinn, Macpeak & Seas

[57] ABSTRACT

An exocellular protease from *Thermomonospora fusca* YX and a process for producing the protease which has the following physicochemical properties:

(1) Molecular mass:

The protease has a molecular mass of from about 10,000 to 14,000 Daltons as measured by SDS-polyacrylamide gel electrophoresis;

(2) Influence of inhibitors:

The protease activity is inhibited by serine protease inhibitors;

(3) Substrate specificity:

A non-specific protease which can hydrolyze food proteins and bovine serum albumin at a rate of 50–100 nmoles peptide bonds/$\mu$g enzyme/minute at 55°, pH 8.5 in 0.5 M Tris buffer without showing any substrate and/or product inhibition;

(4) Reactivity:

A broad spectrum serine type protease having activity at least 5 times greater than trypsin or chymotrypsin towards food grade proteins and bovine serum albumin;

(5) Optimum activity temperature and temperature range:

The optimum activity temperature is 80° C. at pH of 8.0 in 0.05 M Tris buffer at an ionic strength of 0.2 M NaCl; The temperature range is 35° to 95° C. under the same pH, buffer, and ionic strength;

(6) pH range and optimum pH value:

The protease has a pH activity range of from about 7 to 11, and the optimum pH value is 9.0;

(7) Tolerance to ionic strength conditions and optimum ionic strength:

The protease is tolerant to ionic strengths of from 0.0 to about 1.0 M NaCl; Optimum ionic strength is 0.2 M NaCl;

(8) Isoelectric point:

The isoelectric point is at an alkaline pH; and (9) Structure:

The protease is a monomer.

18 Claims, No Drawings ered thereby minimizing undesirable chemical reactions. This is particularly valuable in food processing where nutrients may be lost during processing at high temperatures. In addition, conducting thermal processes at higher temperatures minimizes microbial contamination. This is particularly important for food

ALKALI AND HEAT STABLE PROTEASE FROM THERMOMONOSPORA FUSCA

This is a continuation of application Ser. No. 07/174,168 filed Mar. 28, 1988, which is a continuation-in-part of U.S. Ser. No. 06/930,090 filed Nov. 13, 1986, which is a continuation-in-part of U.S. Ser. No. 06/860,934, filed May 8, 1986, both abandoned.

FIELD OF THE INVENTION

The present invention relates to a novel proteolytic enzyme. In particular, the present invention relates to a novel proteolytic enzyme with broad specificity and alkali and thermal stability. The present invention also relates to a process for preparing the enzyme.

BACKGROUND OF THE INVENTION

Enzymes are being increasingly used in industrial applications and processes. Proteolytic enzymes are valuable ingredients in many reactions required in food processing (e.g., clarification of juices, beer, wine, etc.; tenderization of meats: preparation of hydrolyzed protein materials for food application; preparation of specialized hydrolyzed proteins for special dietary requirements). In addition, proteases are used in detergents which represent a major market. Furthermore, specific proteases may have advantages in facilitating the isolation of high value products produced using modern biotechnology.

It is estimated that enzyme sales for food applications should surpass 0.3 billion dollars in 1986. The market for proteolytic enzymes in detergents is very large and the market in the area of biomedical and biochemical applications is very significant.

However, the application of enzymatic catalysis to fine organic synthesis, medicine, and the food industry is often hindered because many enzymes, when subjected to temperatures higher than those found in their natural environment, become unstable and rapidly inactivate or denature. Hence, the art of enzyme stabilization toward heat denaturation has become the subject of intense interest in recent years. Modification of the heat stability of certain proteins, as in enhancing the thermal stability of some enzymes used in food and beverage manufacture or as in-place-cleaning (IPC) agents for processing equipment, requires an understanding of the relationship between a protein's structure and its inherent thermal stability.

A major obstacle limiting more widespread use of enzymes is their high cost. Reduction in cost may be achieved by more efficient production using biotechnology and by enhancing the stability of enzymes. In this regard, thermostability is a highly desirable trait in enzymes for the food biomedical, and detergent industry. Thermostability connotes the retention of enzyme activity upon exposure to temperatures above 60° C. for prolonged periods.

Thermostability is desirable because the efficiency of enzymes is markedly improved at higher temperatures. Thus, less enzyme is required in particular applications. Also, holding times for specific processes can be shortened thereby minimizing undesirable chemical reactions. This is particularly valuable in food processing where nutrients may be lost during processing at high temperatures. In addition, conducting thermal processes at higher temperatures minimizes microbial contamination. This is particularly important for food safety and for preparation of special hydrolyzed products for therapeutic diets.

In addition to thermal stability, broad substrate specificity and pH tolerance, particularly tolerance to alkaline pH values, are very desirable traits for many food processing applications but more importantly, for enzymes to be used in the detergent industry. For use in detergents, it is desirable to have a thermostable alkaline tolerant broad specificity type of protease which makes it compatible with the alkaline detergents and the temperature of warm washing water.

SUMMARY OF THE INVENTION

Accordingly, one object of the present invention is to provide an exocellular protease having thermal stability, broad substrate specificity and broad pH tolerance.

These and other objects are achieved by providing an exocellular protease from *Thermomonospora fusca* YX (family Thermomonosporaceae) having the following physicochemical properties:

(1) Molecular mass:

The protease has a molecular mass of from about 10,000 to 14,000 Daltons as measured by SDS polyacrylamide gel electrophoresis:

(2) Influence of inhibitors:

The protease activity is inhibited by serine protease inhibitors:

(3) Substrate specificity:

A non-specific protease which can hydrolyze food proteins and bovine serum albumin at a rate of 50–100 nmole peptide bonds/minute/$\mu$g enzyme at 55° C., pH 8.5 in 0.05M Tris buffer without showing any substrate and/or product inhibition;

(4) Reactivity:

A broad spectrum serine type protease having activity at least 5 times greater than trypsin or chymotrypsin towards food grade proteins and bovine serum albumin;

(5) Optimum activity temperature and temperature range:

The optimum activity temperature is 80° C. at a pH of 8.0 in 0.05M Tris buffer at an ionic strength of 0.2M NaCl; The temperature range is 35° to 95° C. under the same pH, buffer and ionic strength;

(6) pH range and optimum pH value:

The protease has a pH activity range of from about 7 to 11 and the optimum pH value is 9.0;

(7) Tolerance to ionic strength conditions and optimum ionic strength:

The protease is tolerant to ionic strengths of from 0.0 to about 1.0M NaCl Optimum ionic strength is 0.2M NaCl;

(8) Isoelectric point:

The isoelectric point is at an alkaline pH; and (9) Structure:

The protease is a monomer.

The present invention also provides a process for producing exocellular protease from *Thermomonospora fusca* YX which comprises cultivating an exocellular protease producing *Thermomonospora fusca* YX or a variety or clone or mutant thereof in culture medium containing cellulose as a main carbon source, a nitrogen source, and normal salts, and recovering the protease from the culture medium.

DETAILED DESCRIPTION OF THE INVENTION

Enzyme Source and Production

The protease of the present invention is produced and secreted by species of the genus Thermomonospora sp (e.g. *Thermomonospora fusca*). Variants and mutants of Thermomonospora sp and related species and mutants can also be used in the present invention as long as the microorganisms secrete the protease. These are known, fully accessible microorganisms naturally occurring in rotting vegetable matter. *Thermomonospora fusca* is a preferred species, and *Thermomonospora fusca* YX is especially preferred. In fact, to date, *Thermomonospora fusca* YX is the only strain actually demonstrated to produce and secrete the protease. *Thermomonospora fusca* YX has been deposited with the American Type Culture Collection in Rockville. Md. and has Accession No. ATCC 53729.

These microbes are thermophilic microbes which can be cultured under aerobic conditions in a media which contains a carbon source, a nitrogen source, and normal salts.

As a main carbon source, cellulose is preferred. The amount of cellulose used is in the range of 0.5 to 5 wt %, preferably 1 wt %.

Examples of other supplemental, but inferior carbon sources include cellobiose and glucose. These are used in a range of from 0.5 to 5 wt %.

Further, although the microbes will grow on carbon sources other than cellulose, the microbes only produce and secrete the protease of the present invention when cellulose is used as the main carbon source in the concentrations mentioned above.

Suitable nitrogen sources include ammonium sulfate, yeast extract, and amino acids.

The ammonium sulfate is used in an amount of about 0.31 wt %. The yeast extract is used in an amount of about 0.1 wt %. The amino acids, if used, are added in amounts readily determined by one skilled in the art.

Suitable examples of normal salts include $ZnSO_4$, $FeSO_4$, $MnSO_4$, $CaCl_2$, NaCl, $MgSO_4$, $KH_2PO_4$ and $K_2HPO_4$.

The normal salts are added at a concentration of from 0.0008 wt % to 0.006 wt %.

Other nonessential nutrients that can be added to the media include vitamins (E.G. biotin, thiamin, etc.). The vitamins are used in amounts of about 1 mg/liter.

A suitable culture time is 35–48 hours, with enzyme production reaching its maximum around 30–40 hours.

The microbe grows best and produces the highest level of protease when cultured under aerobic conditions in the presence of cellulose as the principle carbon source in media containing appropriate salts and growth factors (which may be derived from hydrolyzed yeast) such as amino acids and yeast extracts and at 55° C. In cultures employing cellulose as a principle carbon source, protease activity can be detected after approximately 24 hours with levels increasing up to 48 hours.

The organisms of the present invention grow best at about 50° to 60° C., preferably 55° C., under aerobic conditions in the presence of cellulosic materials. During growth, the protease is secreted into this culture medium from which it can be subsequently isolated.

The protease can be recovered from the culture medium by ammonium sulfate precipitation and further refined by chromatographic columns containing dextran based separation materials. The enzyme can be further purified using cation exchange materials. All separation and purification procedures can be performed in buffered solutions, pH 8, at 6° C. The enzyme is successfully stored for 18 months, and possibly up to at least 2 years, when frozen in liquid nitrogen and stored at −70° C. in water or at −20° C. in ammonium sulfate solution, 10%, following freeze drying, which can be carried out by known methods.

The ammonium sulfate precipitation desalting, and further purification of the protease can be carried out by known methods such as slowly adding $NH_4SO_4$ to the enzyme solution to a concentration of 44% to precipitate the protease which is recovered by centrifugation, redissolved in buffer and desalted by passing the enzyme through a dextran column in Tris buffer (0.05M) and then the eluant containing the protease in 50 mM Tris buffer, pH 8.0, is passed through a cation exchange column equilibrated in the same buffer. The protease retained on the column is eluted using a sodium chloride gradient, 0 to 0.5M NaCl, in the same buffer.

Any cation ion exchange material, e.g., CM-sephadex, CMC-cellulose, sephadex ion exchange, can be used for the further purification of the protease by known methods.

Protease Properties

The exocellular protease has a low molecular mass in the range of from about 10,000 to 14,000 Daltons, as measured by SDS-polyacrylamide gel electrophoresis. When determined by high pressure liquid chromatography (HPLC) or mass spectroscopy, the protease has a molecular mass of about 19,000 Daltons.

The protease activity is inhibited by serine protease inhibitors such as phenylmethane sulfonyl fluoride (PMSF) under known assay conditions.

Based on the activity inhibition studies, the protease can be classified as a broad spectrum serine type of protease. Further, the protease is a non-specific protease because it can effectively and rapidly hydrolyze bovine serum albumin and food proteins, including casein, soy proteins, and egg white proteins, etc.

The hydrolysis occurs at a rate of 50 nmoles peptide bonds/µg enzyme/minute to 100 nmoles peptide bonds/µg enzyme/minute at 55° C., pH 8.5 in the absence of buffer without showing any substrate and/or product inhibition. This latter point is especially important for proteases which are to be used in detergents.

The reactivity of this protease is at least 5 times greater and can be at least 30 times greater than trypsin or chymotrypsin towards bovine serum albumin and food grade protein substrates such as casein, soy proteins, milk proteins, egg white proteins and other food proteins depending upon incubation conditions which one of ordinary skill in the art can readily determine. Reactivity has also been observed in the range of from 5 to 10 times greater than trypsin or chymotrypsin towards the above-mentioned substrates.

Examples of the activity of this protease compared to that of trypsin and chymotrypsin include bovine serum albumin, (activity 5 to 30 times greater than trypsin) and casein (activity 5 to about 30 times greater than trypsin). The activity is measured by known assay conditions.

Significantly, the optimum activity temperature of the enzyme is about 80° C. at pH 8.0, 0.05M Tris buffer and at an ionic strength of 0.2M NaCl. However, the enzyme is active over a temperature range of from 35° to 95° C. under the conditions listed above.

The optimum pH is 9.0 in 0.0–0.2M NaCl, 0.05M Tris, but the enzyme shows a broad pH activity range from 7 to 11.

Additionally, the enzyme is tolerant to a wide range of ionic strength conditions. Specifically, the enzyme will tolerate a range of ionic strengths from 0.0 to about 1.0M NaCl, and the optimum ionic strength is 0.2M NaCl in 0.05M Tris, at 65° C., pH 8.0 and 9.0.

The isoelectric point is at an alkaline pH as determined by cationic behavior and isoelectric focussing. More particularly, the isoelectric point occurs at a pH of 9.2.

Additionally, the protease is a monomer at pH 8.0 as determined by HPLC and SDS-polyacrylamide gel electrophoresis.

This enzyme is remarkable because of its small size, its extremely high thermostability, and its optimum alkaline pH. These features make it extremely suitable for use: a) in detergents, b) for the preparation of protein hydrolysates, c) as a component of cleaning agents for IPC (in-place-cleaning) systems, and d) for cleaning defouling of ultrafiltration membranes. These are important applications particularly in the food and pharmaceutical industries where automated processing is becoming increasingly prevalent and consequently the need for effective IPC agents is becoming more urgent. In addition, this enzyme obviously has potential applications in deproteinizing materials for industrial applications, e.g., clarification of beverages (beer, wine, juices, etc.), deproteinizing cellulosic materials, meat tenderization, etc.

The protease is used for its various applications according to standard protocols of the trade.

The invention will now be described by means of specific examples which are not meant to be limiting.

EXAMPLE 1

Thermomonospora sp, specifically *T. fusca* YX, cultures were cultured initially in tubes containing Hagerdal media and cellulose (filter paper strips) in an amount of a 1 cm×6 cm strip. Cultures were transferred to 100 ml shaker flasks containing Hagerdal media with cellulose substrate in an amount of 0.5 wt % and allowed to multiply. The cultures (100 ml) were inoculated into a 10 liter fermentor (or larger) containing Hagerdal media containing cellulose substrate in an amount of 0.5 wt % and cultured at 55° C. with aeration at 2 L/min and stirring at 300 rpm for 42 hours.

The crude secreted protease was initially recovered by removing cellulose and cells using a centrifuge or separator. The filtrate was then cooled to 2° C. and brought to 45 wt % saturation with $(NH_4)_2SO_4$. The precipitate containing protease was sedimented using a centrifuge at 6000 rpm for 15 minutes.

The pellet was redissolved in a minimal volume of 50 mM Tris pH 8.0 buffer and applied to a G25 Sephadex column for desalting purposes using a 50 mM Tris pH 8.0 as eluant. The protease in the void volume was then applied to a cation exchange (CM Sephadex) column and the pure protease eluted using a 50 mM Tris pH 8.0 buffer with NaCl gradients (0 to 0.5M NaCl). The protease was lyophilized, redissolved in a minimal volume of $H_2O$, desalted on a G15 Sephadex column and stored at −70° C. in water.

Analysis of the protease revealed the following properties:

(1) Molecular mass: 10–14,000 Daltons, as determined by SDS-polyacrylamide gel electrophoresis.

(2) Influence of inhibitors: the protease was inhibited by PMSF.

(3) Substrate specificity: the protease hydrolyzed casein, bovine serum albumin, soy proteins and β-lactoglobulin.

(4) Reactivity: the protease had activity against casein, bovine serum albumin, soy proteins, and β-lactoglobulin at least 5 times greater than trypsin and chymotrypsin.

(5) Optimum reaction temperature: 80° C. at pH 8.0 in 0.05M Tris buffer at an ionic strength of 0.2M NaCl.

(6) Optimum pH value: 9.0 in 0.0 to 0.2M NaCl, 0.05M Tris.

(7) Optimum ionic strength: 0.2M NaCl in 0.05M Tris at 65° C., pH 8.0 and 9.0.

(8) Isoelectric point: alkaline, specifically pH 9.2.

(9) Structure: the protease is monomeric at pH 8.0 as determined by HPLC and SDS-polyacrylamide gel electrophoresis.

EXAMPLE 2

The procedure of Example 1 was repeated using another culture of *T. fusca* YX.

Analysis of the protease revealed the same properties as found in Example 1 except that the reactivity (4) was such that the protease had activity against casein, bovine serum albumin, soy proteins, and β-lactoglobulin up to at least 30 times greater than trypsin and chymotrypsin.

While the invention has been described in detail and with reference to specific embodiments thereof, it will be apparent to one skilled in the art that various changes and modifications can be made therein without departing from the spirit and scope thereof.

What is claimed is:

1. An exocellular protease from *Thermomonospora fusca* YX having the following physicochemical properties:

(1) Molecular mass:
The protease has a molecular mass of from about 10,000 to 14,000 Daltons as measured by SDS-polyacrylamide gel electrophoresis;

(2) Influence of inhibitors:
The protease activity is inhibited by serine protease inhibitors;

(3) Substrate specificity:
A non-specific protease which can hydrolyze food proteins and bovine serum albumin at a rate of 50–100 nmoles peptide bonds/μm enzyme/minute at 55° C., pH 8.5 in 0.05M Tris buffer without showing any substrate and/or product inhibition;

(4) Reactivity:
A broad spectrum serine type protease having activity at least 5 times greater than trypsin or chymotrypsin towards bovine serum albumin and food proteins;

(5) Optimum activity temperature and temperature range:
The optimum activity temperature is 80° C. at a pH of 8.0 in 0.05M Tris buffer at an ionic strength of 0.2M NaCl; The temperature range is 35° to 95° C. under the same pH, buffer and ionic strength;

(6) pH range and optimum pH value:
The protease has a pH activity range of from about 7 to 11, and the optimum pH is 9.0;

(7) Tolerance to ionic strength conditions and optimum ionic strength:

The protease is tolerant to ionic strengths of from 0.0 to about 1.0M NaCl; Optimum ionic strength is 0.2M NaCl;

(8) Isoelectric point:

The isoelectric point is at an alkaline pH; and (9) Structure:

The protease is a monomer.

2. The protease of claim 1, wherein the molecular mass is about 19,000 Daltons as measured by high pressure liquid chromatography and mass spectroscopy.

3. The protease of claim 1, wherein the isoelectric point is at pH 9.2.

4. The protease of claim 1, wherein the reactivity is at least 5 to 10 times greater than trypsin or chymotrypsin towards bovine serum albumin and food proteins.

5. The protease of claim 1, wherein the reactivity is at least 30 times greater than trypsin or chymotrypsin towards bovine serum albumin and food proteins.

6. The protease of claim 1, wherein the serine protease inhibitor is phenylmethane sulfonyl fluoride.

7. The protease of claim 1, wherein the food protein for substrate specificity is casein, soy protein or egg white proteins.

8. The protease of claim 4, wherein the food protein for substrate specificity is casein, soy protein or egg white proteins.

9. The protease of claim 5, wherein the food protein for substrate specificity is casein, soy protein or egg white proteins.

10. The protease of claim 1, wherein the food protein for reactivity is casein, soy proteins, or milk proteins.

11. The protease of claim 4, wherein the food protein for reactivity is casein, soy proteins, or milk proteins.

12. The protease of claim 5, wherein the food protein for reactivity is casein, soy proteins, or milk proteins.

13. A process for producing exocellular protease from *Thermomonospora fusca*, which comprises cultivating an extracellular protease producing *Thermomonospora fusca* YX or a variety or clone or mutant thereof in culture medium containing cellulose as a main carbon source, a nitrogen source, and normal salts and recovering the protease from the culture medium.

14. The process of claim 13, wherein the nitrogen source is ammonium sulfate, yeast extract, amino acids or mixtures thereof.

15. The process of claim 13, wherein the cultivation is carried out under aerobic conditions at a temperature of about 50° to 55° C.

16. The process of claim 13, wherein the protease is recovered from the culture broth by ammonium sulfate precipitation.

17. The process of claim 16, wherein the protease is desalted by chromatography.

18. The process of claim 17, wherein the protease is further purified by cation exchange chromatography.

* * * * *